United States Patent
Sinn Blandy et al.

(10) Patent No.: US 11,650,200 B2
(45) Date of Patent: *May 16, 2023

(54) DEVICE FOR WHOLE BLOOD SEPARATION

(71) Applicant: Quidel Corporation, San Diego, CA (US)

(72) Inventors: Irene Sinn Blandy, San Diego, CA (US); Rayna Thiesen, San Diego, CA (US); Scott Alexander Fall, San Diego, CA (US); Robert Reed, Carlsbad, CA (US); Robert Weiller, Encinitas, CA (US)

(73) Assignee: Quidel Corporation, San Diego, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 17/138,466

(22) Filed: Dec. 30, 2020

(65) Prior Publication Data

US 2021/0116438 A1  Apr. 22, 2021

Related U.S. Application Data

(63) Continuation of application No. 15/815,480, filed on Nov. 16, 2017, now Pat. No. 10,908,145.

(Continued)

(51) Int. Cl.
*G01N 33/50* (2006.01)
*B01L 3/00* (2006.01)
*G01N 33/49* (2006.01)

(52) U.S. Cl.
CPC .......... *G01N 33/5002* (2013.01); *B01L 3/502* (2013.01); *B01L 3/5082* (2013.01);
(Continued)

(58) Field of Classification Search
CPC .. G01N 33/5002; G01N 33/491; B01L 3/502; B01L 3/5082; B01L 2200/0689;
(Continued)

(56) References Cited

U.S. PATENT DOCUMENTS 3,322,114 A   5/1967 Portnoy et al.
5,376,337 A  12/1994 Seymour
(Continued)

FOREIGN PATENT DOCUMENTS

EP       0436897 A2    7/1991
WO   WO 2009/118444 A1  10/2009
(Continued)

OTHER PUBLICATIONS

International Search Report from International Application No. PCT/US2017/061963 dated Jan. 24, 2018, 5 pages (2018).

*Primary Examiner* — Dennis White
(74) *Attorney, Agent, or Firm* — McDermott Will & Emery LLP; Judy M. Mohr; Brennen P. Baylor (57) ABSTRACT

Separation of the cellular components of whole blood, or other biological fluid, from plasma or serum can be achieved for assay analysis. A device for facilitating separation can include, for example, a capillary tube that accurately draws target blood volume, a pad that chemically interacts with red-blood cells, such that the red blood cells become chemically and/or physically trapped within pad material, a mechanism for plasma recovery from the pad upon diffusion or active mixing, and a dropper tip that facilitates dispensing the mixture onto a test device. The treatment of the cellular components can be performed prior to contact with a buffer solution, so release of the cellular components into the buffer solution is reduced or prevented. Additional filtration can be provided to filter any remaining cellular components in the mixture.

15 Claims, 9 Drawing Sheets

Related U.S. Application Data (60) Provisional application No. 62/464,331, filed on Feb. 27, 2017, provisional application No. 62/423,062, filed on Nov. 16, 2016.

(52) U.S. Cl.
CPC ....... *G01N 33/491* (2013.01); *B01D 2215/00* (2013.01); *B01D 2221/10* (2013.01); *B01D 2239/0407* (2013.01); *B01L 2200/0689* (2013.01); *B01L 2300/047* (2013.01); *B01L 2300/0681* (2013.01); *B01L 2300/0832* (2013.01); *B01L 2300/0838* (2013.01); *B01L 2300/123* (2013.01); *B01L 2300/161* (2013.01); *B01L 2400/0406* (2013.01); *B01L 2400/0481* (2013.01); *B01L 2400/0683* (2013.01)

(58) Field of Classification Search
CPC ..... B01L 2400/0683; B01L 2400/0481; B01L 2300/161; B01L 2300/047; B01L 2300/123; B01L 2300/0832; B01L 2300/0681; B01L 2300/0838; B01L 2400/0406; B01D 2239/0407; B01D 2221/10; B01D 2215/00
See application file for complete search history.

(56) References Cited

U.S. PATENT DOCUMENTS

| | | |
|---|---|---|
| 10,908,145 B2 | 2/2021 | Sinn Blandy et al. |
| 2004/0018575 A1 | 1/2004 | Rappin et al. |
| 2004/0161788 A1 | 8/2004 | Chen et al. |
| 2010/0093551 A1 | 4/2010 | Montagu |
| 2018/0345276 A1 | 12/2018 | Iwasawa et al. |

FOREIGN PATENT DOCUMENTS

| | | |
|---|---|---|
| WO | WO 2015/191777 A2 | 12/2015 |
| WO | WO 2016/073415 A2 | 5/2016 |
| WO | WO 2016/147748 A1 | 9/2016 |

DEVICE FOR WHOLE BLOOD SEPARATION

CROSS-REFERENCE TO RELATED APPLICATIONS

This application is a continuation of U.S. patent application Ser. No. 15/815,480, filed Nov. 16, 2017, now allowed, which claims the benefit of U.S. Provisional Application No. 62/423,062, filed Nov. 16, 2016, and U.S. Provisional Application No. 62/464,331, filed Feb. 27, 2017, the entirety of each of which is incorporated herein by reference.

TECHNICAL FIELD

The present disclosure generally relates to separation of cellular components from a biological sample, such as separation of whole blood into blood cells and plasma.

BACKGROUND

Various techniques can be employed to analyze body fluids for the presence or absence of a particular soluble constituent. For example, tests are available to detect glucose, uric acid or protein in urine, or to detect glucose, triglycerides, potassium ion or cholesterol in blood. Devices and methods to process body fluids prior to testing are used, for example, to separate the fluid sample into separate portions or fractions. For example, cellular components of whole blood can be separated from the plasma or serum for use in an assay to test for a particular soluble constituent. The resulting plasma or serum can be examined for a response to provide a prompt and accurate qualitative or quantitative assay for one or more soluble constituents of the plasma or serum.

BRIEF SUMMARY

The subject technology is illustrated, for example, according to various aspects described below.

According to some embodiments of the present disclosure, a kit can include: a container including a reservoir for receiving a solution; a sample device including: an inflow chamber for receiving a liquid sample; a mixing chamber; a pad between the inflow chamber and the mixing chamber, the pad optionally including a processing reagent such as a red blood cell agglomerating substance; an outflow port adjacent to the mixing chamber; and an interface for sealably connecting the sample device to the container such that the reservoir is in fluid communication with the mixing chamber.

The inflow chamber can include a capillary tube. The sample device further can include a filter between the mixing chamber and the outflow port. The kit can further include a solution within the reservoir.

According to some embodiments of the present disclosure, a method can include: with an inflow chamber of a sample device, receiving a liquid sample; facilitating separation of a first portion of the liquid sample from a second portion of the liquid sample by retaining the second portion at a pad, the pad optionally including a processing reagent such as red blood cell agglomerating substance when the liquid sample is, for example, blood; facilitating flow of the first portion of the liquid sample through the pad and to a mixing chamber; sealably connecting the sample device to a container including a reservoir containing a buffer solution; mixing the first portion of the liquid sample with the buffer solution to create a mixture; and dispensing at least some of the mixture from the mixing chamber and through an outflow port of the sample device.

The dispensing can include deforming at least a portion of the sample device or the container to increase a pressure within the mixing chamber. The dispensing can include facilitating flow through a filter between the mixing chamber and the outflow port. The dispensing can also comprise applying a directional force to the sample device or the container to effect release of at least some of the mixture.

According to some embodiments of the present disclosure, a kit can include: a sample device including: a pad for receiving a liquid sample, the pad optionally including a processing reagent, such as a red blood cell agglomerating substance; and a chamber having an outflow port; and a container including: a reservoir containing or configured to contain a solution; and an interface for sealably connecting the sample device to the container such that the reservoir is in fluid communication with the chamber.

The kit can further include a collection device for collecting the liquid sample, such as a blood sample or a urine sample or a sputum sample from a patient. The collection device can include a capillary tube and a bulb in fluid communication with the capillary tube.

According to some embodiments of the present disclosure, a method can include: with a pad of a sample device, receiving a liquid sample, the pad optionally including a processing reagent such as a red blood cell agglomerating substance; sealably connecting the sample device to a container including a reservoir containing or configured to contain a solution; facilitating separation of a first portion of the liquid sample from a second portion of the liquid sample by retaining the second portion at the pad; mixing the first portion of the liquid sample with the solution to create a mixture in a chamber of the sample device; and dispensing at least some of the mixture from the chamber and through an outflow port of the sample device.

The dispensing can include deforming at least a portion of the sample device or the container to increase a pressure within the chamber. The dispensing can include facilitating flow through a filter between the chamber and the outflow port. The dispensing can also comprise applying a directional force to the sample device or the container to effect release of at least some of the mixture. The method can further include collecting the liquid sample with a capillary tube of a collection device for collecting the liquid sample, for example a blood sample from a patient, and receiving the liquid sample can include dispensing the sample from the capillary tube by deforming at least a portion of a bulb in fluid communication with the capillary tube.

According to some embodiments of the present disclosure, a kit can include: a container including: a reservoir containing or configured to contain a solution; a mixing chamber; a barrier separating the reservoir from the mixing chamber; a sample device including: an inflow chamber for receiving a liquid sample; a channel; a pad between the inflow chamber and the channel, the pad optionally including a processing reagent such as a red blood cell agglomerating substance; a dispenser including: an outflow port; an interface for sealably connecting the dispenser to the container such that the mixing chamber is in fluid communication with the outflow port, wherein the dispenser is configured to urge the sample device through the barrier when the dispenser is connected to the container.

The inflow chamber can include a capillary tube. The dispenser further can include a filter that is between the mixing chamber and the outflow port when the dispenser is connected to the container. The container can include at least one protrusion to secure at least a portion of the sample device within the mixing chamber.

According to some embodiments of the present disclosure, a method can include: with an inflow chamber of a sample device, receiving a liquid sample while at least a portion of the sample device is within a container; facilitating separation of a first portion of the liquid sample from a second portion of the liquid sample by retaining the second portion at a pad, the pad optionally including a processing reagent such as a red blood cell agglomerating substance; with a dispenser, urging the sample device through a barrier separating a reservoir of the container from a mixing chamber of the container; sealably connecting the dispenser to the container; mixing the first portion of the liquid sample with a solution in the reservoir to create a mixture; and dispensing at least some of the mixture from the mixing chamber and through an outflow port of the sample device.

The dispensing can include deforming at least a portion of the container to increase a pressure within the mixing chamber. The dispensing can include facilitating flow through a filter between the mixing chamber and the outflow port. The dispensing can also comprise applying a directional force to the sample device or the container to effect release of at least some of the mixture.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The cellular components of whole blood, and especially the red blood cells, are the primary interfering substances in assays for a soluble constituent of whole blood. Many blood tests are chromogenic, wherein a soluble constituent of the whole blood interacts with a particular reagent either to form a uniquely-colored complex or derivative as a qualitative indication of the presence or absence of the constituent, or to form a colored complex or derivative of variable color intensity as a quantitative indication of the presence of the constituent. The deep red color of the whole blood sample substantially interferes with these chromogenic tests, and therefore the highly-colored red blood cells usually are separated from the plasma or serum before the blood sample is assayed for a particular soluble constituent. The presence of red blood cells also can interfere with various nonchromogenic blood assays, whereby the assay results are either inconsistent or, if consistent, are inaccurate. Furthermore, other cellular components, including the white blood cells, also can interfere in standard chromogenic blood assays.

Conventionally, plasma or serum can be separated from the cellular material of whole blood by centrifugation or by clotting. The cellular material collects at the bottom of the centrifuge or sample tube and the supernatant plasma or serum is decanted. Accordingly, the interfering cellular components of whole blood are sufficiently removed such that a substantial background interference is avoided. However, the centrifuge method requires a large blood sample, a long centrifuge time, and appropriate equipment. Furthermore, the centrifuge method requires several manipulative steps. The clotting method of obtaining serum requires a long time (30-60 minutes) for clotting to occur and centrifugation may be required after clotting occurs.

Other techniques can involve test strips for lateral flow of samples for analysis. However, in some designs, red blood cells form aggregates or blockages within the chemical strip that disrupt the lateral flow. Such blockages often produce inaccurate and/or invalid results.

Improved techniques to efficiently separate and accurately assay small volumes of whole blood are described herein. A separation technique can shield the technician from contact with the blood sample, avoid time delays, and yield accurate and reproducible results. Techniques based on the present disclosure can allow the safe, accurate, and economical assay of a whole blood, or other biological fluid, sample for a particular soluble component to achieve essentially total separation of the cellular components of whole blood from the plasma or serum. It will be appreciated that the systems and devices and methods described herein are contemplated for use with a variety of fluid samples, and whilst the description herein uses blood as a model sample, the systems and devices and methods may also be used with other fluid samples.

Embodiments of the present disclosure can include a single use, disposable device. In one embodiment, the device is a whole blood separator in a fully contained, squeezable container including a dropper. Embodiments described herein for use with a blood sample can include (1) a capillary tube that accurately draws a target blood volume, (2) a pad that chemically interacts with red-blood cells, such that the red blood cells become chemically and/or physically trapped within the pad material, (3) a mechanism for plasma recovery from the pad upon diffusion or active mixing, and (4) a dropper tip that facilitates dispensing the mixture onto a test device. Embodiments of the present disclosure can incorporate a blood capillary tube with a volume monitoring mechanism. Embodiments of the present disclosure can facilitate removal of red-blood cells from a patient venipuncture of finger stick whole blood sample, such that plasma and buffer solution can be added to the test strip. The design can simplify the work-flow for the end-user and can be applied universally across assays that utilize a whole blood sample requiring a plasma matrix.

Chemically or physically capturing the red-blood cells in the pad material improves the efficiency of plasma separation, specifically the efficiency of red blood cell capture in a pad material which requires less solution volume to recover plasma (reduce sample dilution effect) and prevents red blood cells from lysing and/or leaking from the pad onto the test device upon use. The treatment of the red blood cells can be performed prior to contact with a buffer solution, so the red blood cells will not be, or will be minimally, released into the buffer solution when the sample and buffer solution are mixed or when pressure is added to the container to express the sample solution.

Figure 1:
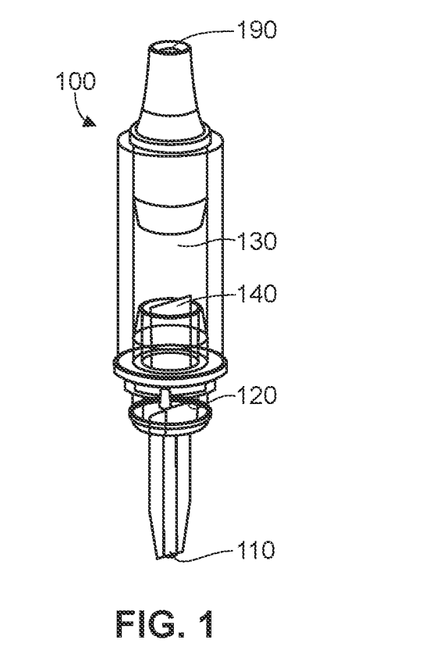
FIG. 1 illustrates a perspective view of a sample device, according to some embodiments of the present disclosure.
Figure 2:
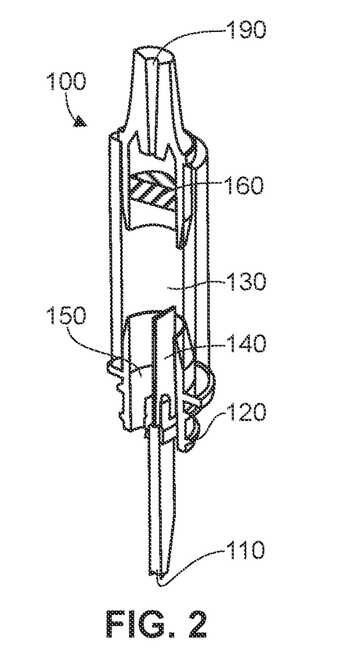
FIG. 2 illustrates a sectional view of the sample device of FIG. 1, according to some embodiments of the present disclosure.

A system can facilitate processing of a fluid or liquid sample, and in particular a whole blood sample from a human patient or other mammal. In one embodiment, the system is for use with a whole blood sample and, as will be shown, it effects separation and dispensation of the plasma while the cellular components are retained in the system. The system can include a sample device for receiving and treating a liquid sample from a patient. FIGS. 1 and 2 illustrate a sample device 100, according to some embodiments of the present disclosure. According to some embodiments, for example as illustrated in FIGS. 1 and 2, the sample device 100 can include an inflow chamber 110 for receiving a sample. The inflow chamber 110 can include a capillary tube with an open end located on a first side of the sample device 100. The inflow chamber 110 can be separated from a mixing chamber 130 by a pad 140. The pad 140 can optionally include a processing reagent, such as an anti-RBC reagent, such as an anti-human red blood cell antibody that is configured to facilitate collection of blood cells therein. The pad 140 can be a fiber or polymer membrane which has pore size larger than a cellular component, e.g., red blood cells, so that the red blood cells enter freely, but smaller than a processed cellular component, e.g., agglutinated red blood cells (e.g., agglutinated by the interaction with anti-human RBC antibody). The sample device 100 can also include a channel 150 that provides fluid communication to the mixing chamber 130 via a pathway other than through the inflow chamber 110 and the pad 140. As described further herein, the channel 150 provides a pathway for reagents after connecting the sample device 100 to a container holding the reagents.

The sample device 100 can also include a filter 160 between the mixing chamber 130 and an outflow port 190. The filter 160 can be configured to allow passage of a first fraction or portion of the liquid sample, such as a plasma fraction of a blood sample, there through while retaining a second fraction or portion of the liquid sample, such as cellular components of a whole blood sample. The filter 160 can include a separation membrane (for example, polysulfone material) with asymmetrical porosity to trap a component of the sample. Alternatively or in combination, the filter 160 can include a filter portion (polymer, glass fiber, woven mesh, etc.) with pore size smaller than a treated or non-treated portion of the liquid sample, such as agglutinated red blood cells, in order to trap any of this portion that may escape pad 140. The thickness of the filter 160 may be selected to obtain the amount of filtration required while retaining a minimum volume of plasma or reagent. The outflow port 190 can be located at an end of the sample device 100 that is opposite the inflow chamber 110 and allow dispensation of a sample portion (e.g., a plasma portion of a blood sample) that is passed from the filter 160. In some embodiments, the filter 160 is not included, and a portion of the sample, (e.g., the cellular components) are retained within the pad 140. The sample device 100 can include a device interface 120 (e.g., threads) that can facilitate connection and securement of the sample device 100 to a container, as further described herein.

Figure 3:
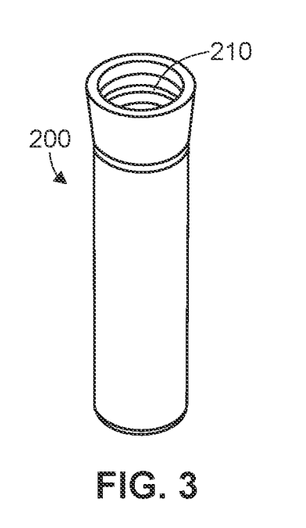
FIG. 3 illustrates a perspective view of a container, according to some embodiments of the present disclosure.
Figure 4:
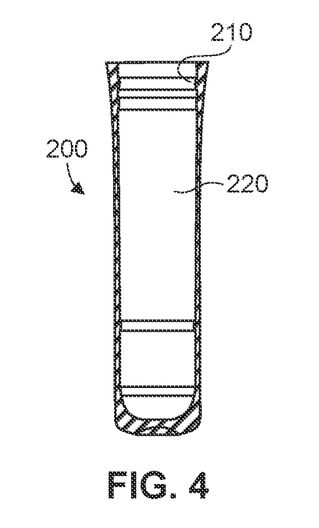
FIG. 4 illustrates a sectional view of the container of FIG. 3, according to some embodiments of the present disclosure.

The system can include a container that helps facilitate mixing of a sample with a reagent. FIGS. 3 and 4 illustrate a container 200, according to some embodiments of the present disclosure. According to some embodiments, for example as illustrated in FIGS. 3 and 4, the container 200 can include a reservoir 220 for holding and/or receiving a reagent, such as a solution containing a liquid, for example a processing solution, water, saline, a buffer, phosphate buffered saline, an electrolytic solution, etc. The reservoir 220 can be placed in fluid communication with at least a portion of the sample device 100, so that a fluid (liquid) from the sample device 100 and a fluid (liquid) from the container 200 can mix. For example, the reservoir 220 can be placed in fluid communication with the mixing chamber 130 of the sample device 100. The container 200 can include a container interface 210 (e.g., threads) that can facilitate connection and securement of the container 200 to the sample device 100. For example, the sample device 100 can be connected to the container 200 by engaging the device interface 120 with the container interface 210. While engaged, the device interface 120 and the container interface 210 maintain a connection between the sample device 100 and the container 200. The device interface 120 and the container interface 210 can also seal a space within the sample device 100 and the container 200 so that materials within the space are separate from an external environment. At least a portion of the container 200 can be deformable, to allow a user to squeeze the container 200 and dispense a fluid, as described further herein.

Figure 5:
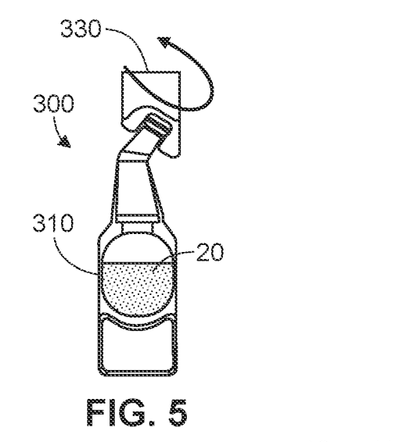
FIG. 5 illustrates a side view of a dispenser, according to some embodiments of the present disclosure.

The system can include substances for use with other components of the system to facilitate separation of the liquid sample into a first portion and a second portion, such as required in whole blood separation. FIG. 5 illustrates a reagent 20, such as a solution containing a solution, within a dispenser 300, according to some embodiments of the present disclosure. According to some embodiments, for example as illustrated in FIG. 5, the dispenser 300 can include a reservoir 310 for holding and/or dispensing a fluid. For example, the dispenser 300 can be ampoule with a predetermined amount of a reagent. The reservoir 310 can be initially sealed by a removable cap 330.

According to embodiments, a kit of parts can include components of the system. For example, one or more kits of parts can include the sample device 100, the container 200, and/or the dispenser 300. Directions for use ("DFU") can be included with the kit. One or more of the sample device 100, the container 200, and the dispenser 300 can be disposable and packaged for one-time use.

Figure 6:
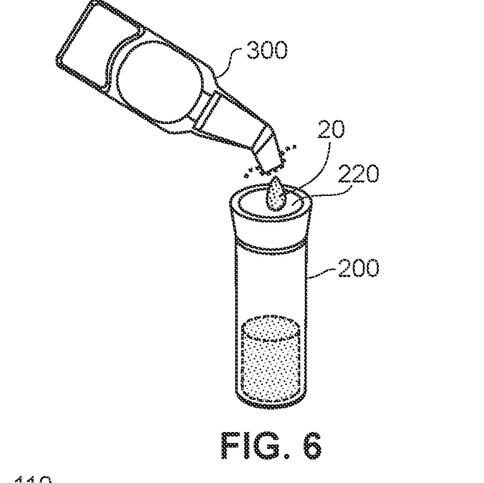
FIG. 6 illustrates a perspective view of the dispenser of FIG. 5 and the container of FIG. 3, according to some embodiments of the present disclosure.

A method can employ components of the system or kit, as described herein, to achieve processing of a liquid sample, such as whole blood separation. According to some embodiments, for example as illustrated in FIG. 6, the reagent 20 can be dispensed from the dispenser 300 and into the reservoir 220 of the container 200. Alternatively, the container 200 is configured to contain a liquid, and the reservoir of the container can be filled with a liquid by an end user of the system or kit.

Figure 7:
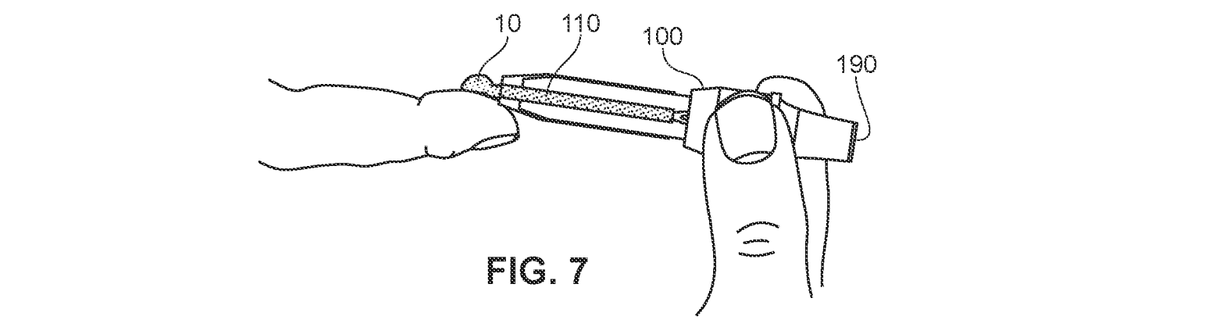
FIG. 7 illustrates a view of the sample device of FIG. 1 receiving a sample, according to some embodiments of the present disclosure.

According to some embodiments, for example as illustrated in FIG. 7, a sample 10, such as blood, can be collected with and into the inflow chamber 110 of the sample device 100. The sample device 100 can be held horizontally or substantially horizontally during filling of the inflow chamber 110. The inflow chamber 110 can automatically cease to collect the sample 10 once the inflow chamber 110 is filled. For example, when the inflow chamber is configured to be a capillary tube, collection can stop when the capillary is full, such that there is no surface left for the liquid sample (e.g., blood) to flow into. At such a saturation point, the inflow chamber 110 will not absorb any more liquid. Accordingly, in one embodiment, the inflow chamber of the sample device is configured as a capillary tube with a defined length that collects a fixed volume of a fluid sample.

Figure 8:
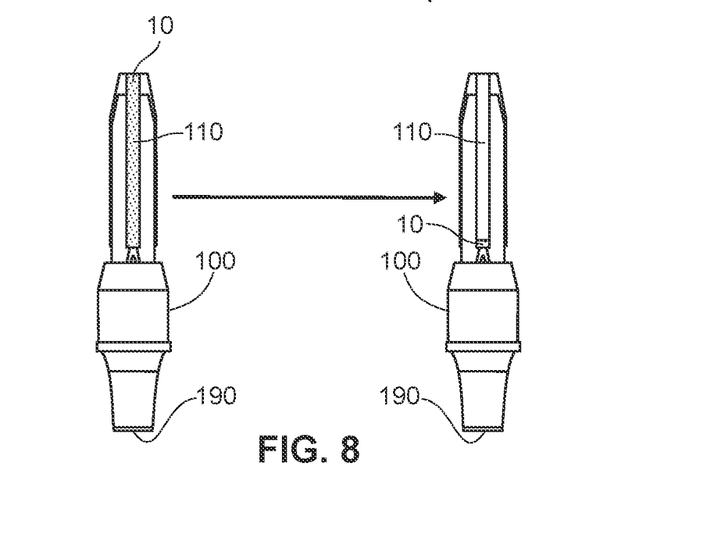
FIG. 8 illustrates a view of the sample device of FIG. 7, according to some embodiments of the present disclosure.

According to some embodiments, for example as illustrated in FIG. 8, the sample device 100 can be positioned vertically with the inflow chamber 110 gravitationally above the mixing chamber 130 (not visible in FIG. 8). While the sample device 100 is in such a position, the sample 10 can be allowed to drain from the inflow chamber 110 and to the pad 140 and/or the mixing chamber 130 (e.g., via the pad 140). As the sample 10 passes through the pad 140, the sample 10 can react with substances within the pad 140, such as anti-RBC antibodies. For example, at least a portion of the sample 10 (e.g., plasma or serum) can be separated from a second portion (e.g., red blood cells) of the sample 10 by retaining the second portion (e.g., red blood cells) at the pad 140. The sample device 100 can be held vertically for an amount of time sufficient to allow the sample 10 to drain out of this inflow chamber 110 (e.g., 10 seconds, 20 seconds, 30 seconds, 40 seconds, 50 seconds, 60 seconds, or more than 60 seconds).

Figure 9:
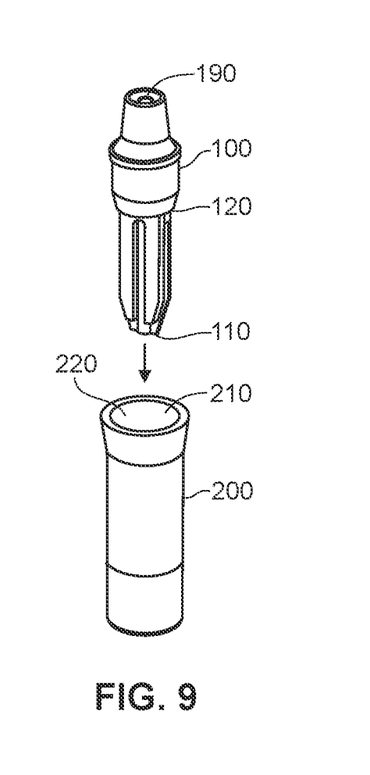
FIG. 9 illustrates a perspective view of the sample device of FIG. 8 and the container of FIG. 3, according to some embodiments of the present disclosure.

According to some embodiments, for example as illustrated in FIG. 9, the sample device 100 can be connected to the container 200. For example, the inflow chamber 110 can be inserted into the reservoir 220 of the container 200. The device interface 120 can engage the container interface 210 to seal a space between the sample device 100 and the container 200. The sample device 100 can be connected to the container 200 in a way that allows the outflow port 190 to be exposed or exposable.

Figure 10:
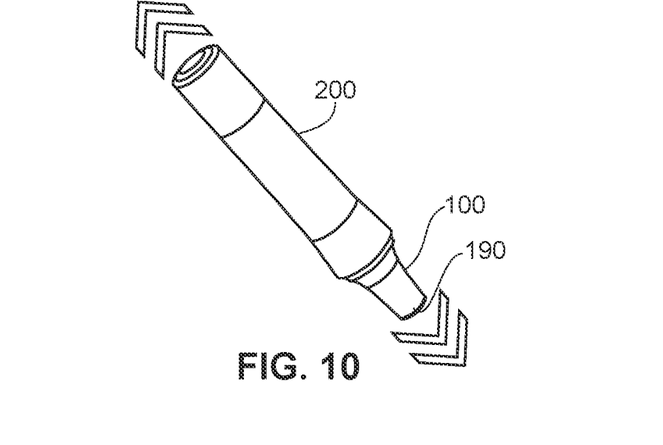
FIG. 10 illustrates a perspective view of the sample device and the container of FIG. 9, according to some embodiments of the present disclosure.

According to some embodiments, for example as illustrated in FIG. 10, the sample device 100 and the container 200 can be agitated and/or shaken to mix at least a portion of the sample 10 in the sample device 100 with at least a portion of the reagent 20 in the container 200. The mixing can occur, at least in part, within the mixing chamber 130. For example, during the mixing, the reagents 20 can pass through the channel 150 to the mixing chamber 130. Within the mixing chamber 130, the reagents can mix with the sample 10 that is on or within the pad 140. The sample device 100 and the container 200 can be agitated and/or shaken manually or by a machine.

Figure 11A:
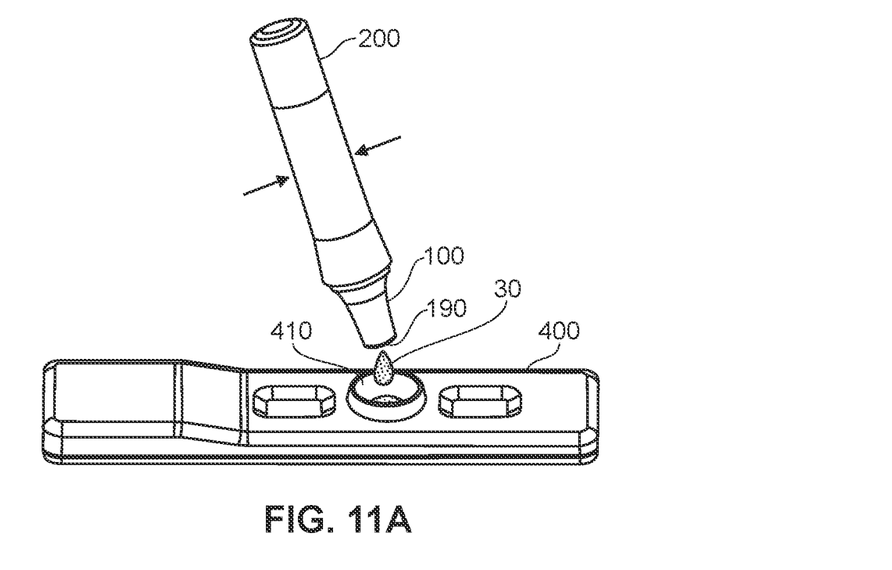
FIGS. 11A-11B illustrate perspective views of the sample device and the container, according to some embodiments of the present disclosure.
Figure 11B:
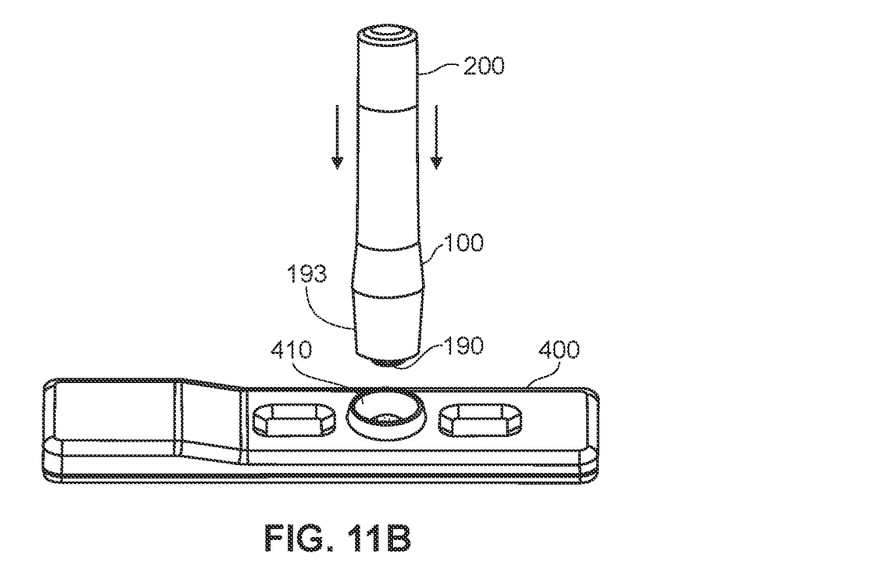

According to some embodiments, for example as illustrated in FIGS. 11A-11B, the mixture produced by the agitation and/or shaking can be dispensed from the sample device 100 and the container 200. The outflow port 190 can be directed toward a receptacle 410 of a cassette 400. In one embodiment, at least a portion of the container 200 and/or the sample device 100 can be deformed to create pressure within the mixing chamber 130, as indicated in FIG. 11A by the arrows. In response to this increased pressure, a portion of the mixture 30 within the mixing chamber 130 can be forced through the filter 160 and dispensed from the outflow port 190. At least a portion of the mixture 30 can be retained within the mixing chamber 130. For example, the cellular components that are too large to fit through the filter 160 can be retained within the mixing chamber 130 while the plasma passes through the filter 160 and the outflow port 190. In another embodiment, as illustrated in FIG. 11B, sample device 100 comprises a skirt 193 surrounding outflow port 190, the skirt configured to engage with an external docking station or sample receiving zone, such as receptacle 410. Mixture 30 is dispensed from the mixing chamber by applying a directional force to the sample device or the container to engage or actuate a mechanism to release the mixture. In one embodiment, the directional force is, with respect to a gravitational frame of reference, a downward force. The downward applied force effects release of the fluid mixture from the sample device. Mechanisms responsive to a downward force applied by a user are referred to as "press and release" or "press to dispense" mechanisms. In one embodiment, dispensing mixture from the mixing chamber comprises applying a directional force to effect release of mixture, wherein substantially all of the mixture in the mixing chamber is dispensed. In other embodiments, greater than 90%, 95%, 98% or 99% of the mixture in the mixing chamber is dispensed.

In one embodiment, a portion or all of an inner surface of outflow port 190 is treated with material that facilitates release of mixture. For example, a hydrophilic material or a hydrophobic material can be applied to or coated on the inner surface of the outflow port, the container, the mixing chamber, or other surfaces of the sample device and container, to modify the surface-liquid mixture surface tension.

Figure 12:
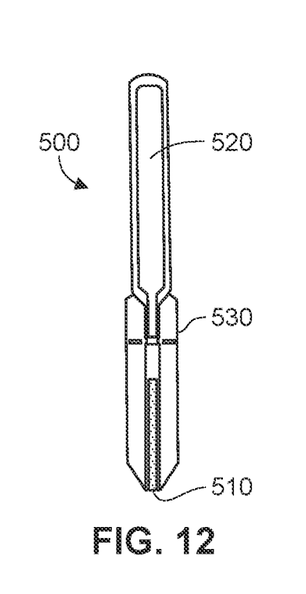
FIG. 12 illustrates a side view of a collection device, according to some embodiments of the present disclosure.

Alternatively or in combination with the above embodiments, systems can facilitate processing of a fluid sample, such as a whole blood sample or sputum sample or urine sample, to separate the sample into a first portion, such as plasma or protein free sputum or urine, and a second sample portion, such as cellular components of blood, protein or cells of sputum or urine, and dispensing of the first portion only from the system—that is, the second portion is retained in the system. According to some embodiments, such a system can include a sample device for receiving a sample from a patient. FIG. 12 illustrates a collection device 500, according to some embodiments of the present disclosure. According to some embodiments, for example as illustrated in FIG. 12, collection device 500 can include an inflow chamber 510 for receiving a sample. The inflow chamber 510 can include a capillary tube with an open end located on a first side of the collection device 500, however it will be appreciated that the inflow chamber need to be a capillary tube but may be of other configurations and geometries. The inflow chamber 510 can be in fluid communication with a compression chamber 520. At least a portion of collection device 500 can be deformable, to facilitate collection of the sample within the inflow chamber under various pressure conditions. The collection device 500 can include a marker 530 to provide a target fill indication along the length of inflow chamber 510. In one embodiment, where the inflow chamber is configured as a capillary tube, the inflow chamber has a defined length for collection of a fixed, known, and/or predetermined volume of sample.

Figure 13:
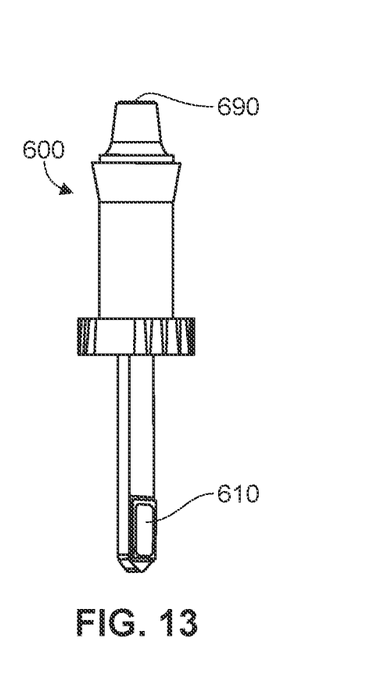
FIG. 13 illustrates a side view of a sample device, according to some embodiments of the present disclosure.
Figure 14:
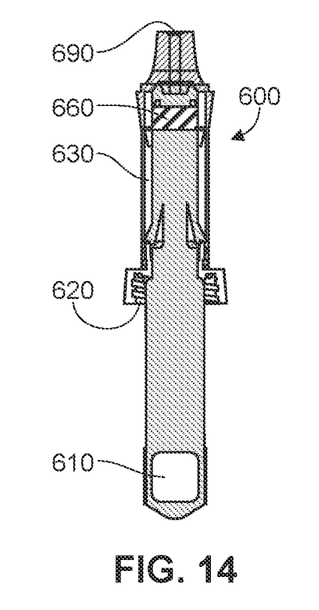
FIG. 14 illustrates a sectional view of the sample device of FIG. 13, according to some embodiments of the present disclosure.

The system can include a sample device for receiving a sample from a patient and/or receiving a sample from the collection device. FIG. 13 illustrates a sample device 600, according to some embodiments of the present disclosure. According to some embodiments, for example as illustrated in FIGS. 13 and 14, the sample device 600 can include a pad 610 for receiving a sample. The pad 610 can include a processing reagent, such as an anti-RBC reagent that is configured to facilitate collection of blood cells therein. The sample device 600 can also include a chamber 630 (visible in FIG. 14) for receiving the sample and/or reagents when connected to a container, as described further herein.

With reference to FIG. 14, the sample device 600 can also include a filter 660 between chamber 630 and an outflow port 690. Filter 660 can be configured to allow passage of a first fraction of the sample, such as plasma, there through while retaining a second fraction of the sample, such as cellular components of the sample. In one embodiment, the filter is a glass fiber filter. Outflow port 690 can be located at an end of sample device 600 that is opposite pad 610 and allow dispensation of that fraction or portion of sample, such as the plasma, that is passed from filter 660. In some embodiments, filter 660 is not included, and the cellular components are retained within pad 610. The sample device 600 can include a device interface 620 (e.g., threads) that can facilitate connection and securement of sample device 600 to a container, as further described herein.

Figure 15:
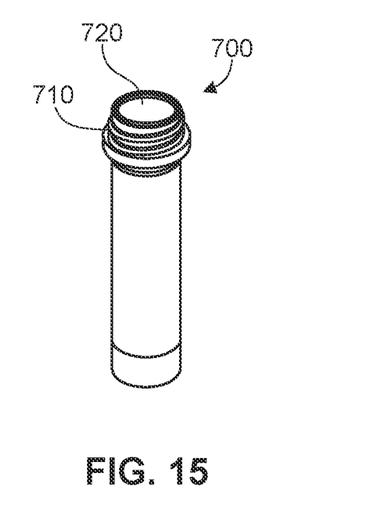
FIG. 15 illustrates a perspective view of a container, according to some embodiments of the present disclosure.

The system can include a container that helps facilitate mixing of a sample with a reagent. FIG. 15 illustrates a container 700, according to some embodiments of the present disclosure. According to some embodiments, for example as illustrated in FIG. 15, container 700 can include a reservoir 720 for holding and/or receiving a fluid or a reagent, such as a solution containing a buffer. Reservoir 720 can be placed in fluid communication with at least a portion of sample device 600, so that a fluid from sample device 600 and a fluid from container 700 can mix. For example, reservoir 720 can be placed in fluid communication with chamber 630 of the sample device 600. The container 700 can include a container interface 710 (e.g., threads) that can facilitate connection and securement of container 700 to sample device 600. For example, sample device 600 can be connected to container 700 by engaging device interface 620 with container interface 710. While engaged, device interface 620 and container interface 710 maintain a connection, preferably a fluid-tight connection, between the sample device and the container. The device interface 620 and the container interface 710 can also seal a space within the sample device 600 and the container 700 so that materials within the space are separate from an external environment. In one embodiment, at least a portion of the container 700 can be deformable, to allow a user to squeeze the container 700 and dispense a fluid, as described further herein.

According to embodiments, a kit of parts can include components of the system. For example, one or more kits of parts can include the collection device 500, the sample device 600, and/or the container 700. Directions for use ("DFU") can be included with the kit. One or more of the collection device 500, the sample device 600, and the container 700 can be disposable and packaged for one-time use.

Figures 16, 17:
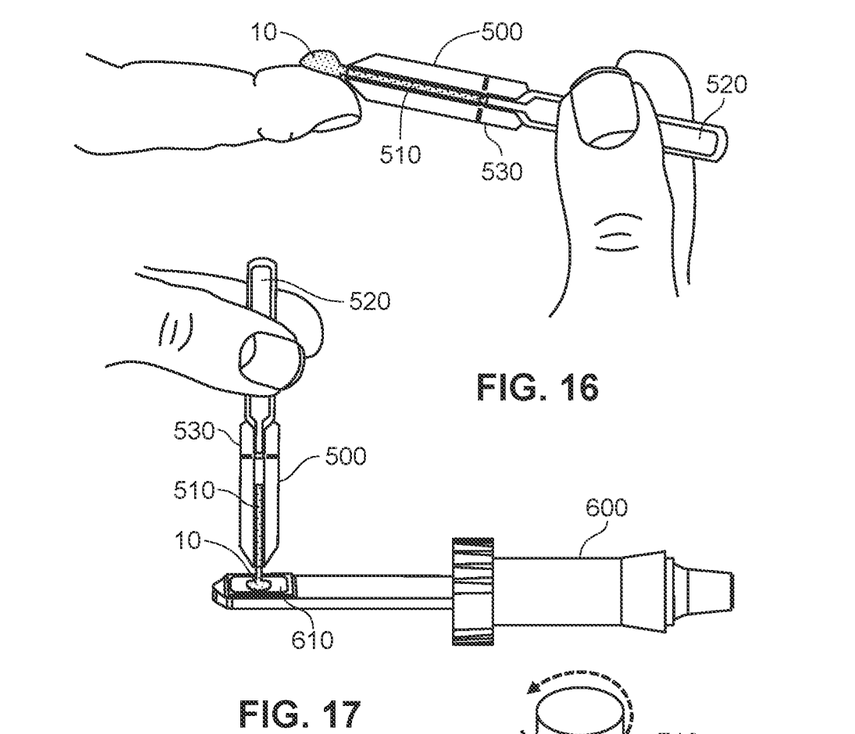
FIG. 16 illustrates a view of the collection device of FIG. 12 receiving a sample, according to some embodiments of the present disclosure.
FIG. 17 illustrates a view of the collection device of FIG. 16 and the sample device of FIGS. 13 and 14, according to some embodiments of the present disclosure.

A method can employ components of the system or kit, as described herein, to achieve processing of a fluid sample, such as processing of a whole blood sample into two portions. According to some embodiments, for example as illustrated in FIG. 16, a sample 10, such as blood, can be collected with and into the inflow chamber 510 of the collection device 500. The collection device 500 can be held horizontally or substantially horizontally during filling of the inflow chamber 510. The compression chamber 520 can be compressed prior to collection and then released to reduce the pressure at the inflow chamber 510 and create flow into the inflow chamber 510. Collection can continue until the sample 10 reaches the marker 530.

According to some embodiments, for example as illustrated in FIG. 17, the collection device 500 can be positioned to dispense all or a portion of the sample 10 to the pad 610 of the sample device 600. The compression chamber 520 can be compressed to increase the pressure at the inflow chamber 510 and create flow out of the inflow chamber 510. The sample 10 can be absorbed into the pad 610. In one embodiment, the collection device is configured to collect a fixed, known, and/or determined volume of sample. In one embodiment, greater than 90%, 95%, 98% or 99% of the sample in the inflow chamber of the collection device is dispensed onto pad 610.

Figure 18:
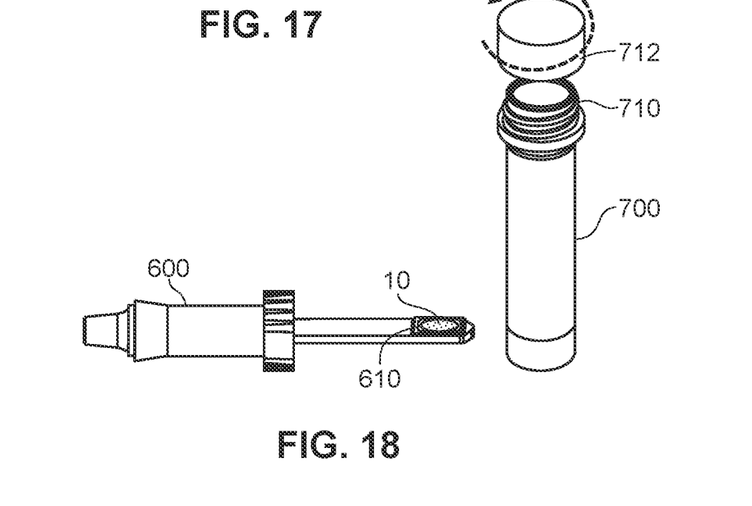
FIG. 18 illustrates a view of the sample device of FIG. 17 and the container of FIG. 15, according to some embodiments of the present disclosure.
Figure 19:
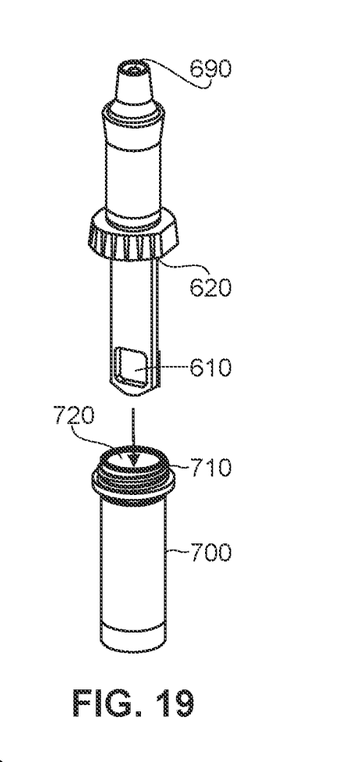
FIG. 19 illustrates a view of the sample device and the container of FIG. 18, according to some embodiments of the present disclosure.

According to some embodiments, for example as illustrated in FIGS. 18 and 19, the sample device 600 can be connected to the container 700. For example, the pad 610 can be inserted into the reservoir 720 of the container 700. The device interface 620 can engage the container interface 710 to seal a space between the sample device 600 and the container 700. The sample device 600 can be connected to the container 700 in a way that allows the outflow port 690 to be exposed or exposable.

Figure 20:
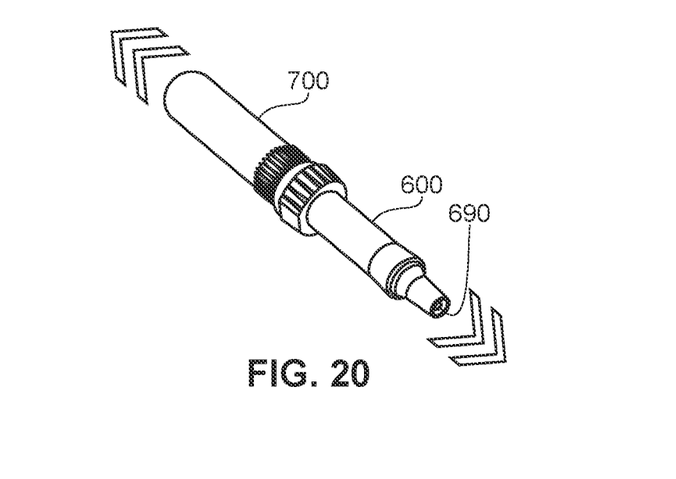
FIG. 20 illustrates a view of the sample device and the container of FIG. 19, according to some embodiments of the present disclosure.

According to some embodiments, for example as illustrated in FIG. 20, the sample device 600 and the container 700 can be agitated and/or shaken to mix at least a portion of the sample 10 in the sample device 600 with at least a portion of the reagents 20 (not shown in FIGS. 18 and 19) in the container 700. The mixing can occur, at least in part, within the chamber 630. Within the chamber 630 and/or the reservoir 720, the reagents 20 can mix with the sample 10 that is on or within the pad 610. The sample device 600 and the container 700 can be agitated and/or shaken manually or by a machine.

Figure 21A:
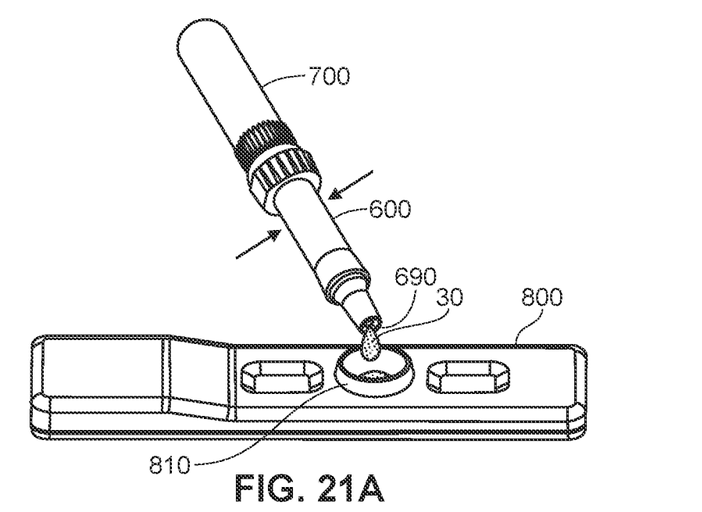
FIGS. 21A-21B illustrate views of the sample device and the container of FIG. 20, for dispensing of all or a portion of the contents, according to some embodiments of the present disclosure.
Figure 21B:
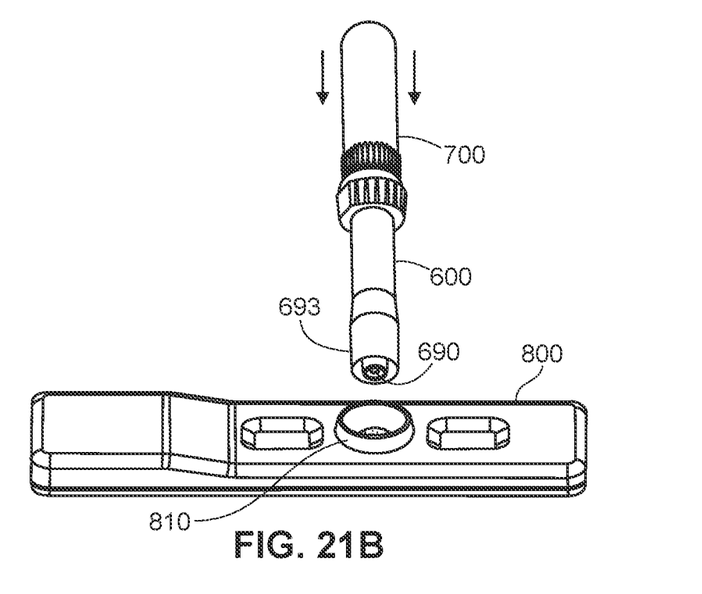

According to some embodiments, for example as illustrated in FIGS. 21A-21B, the mixture produced by the agitation and/or shaking can be dispensed from the sample device 600 and the container 700. The outflow port 690 can be directed toward a receptacle 810 of a cassette 800. In one embodiment, as shown in FIG. 21A, at least a portion of the container 700 and/or the sample device 600 can be deformed to create pressure within the chamber 630. In response to this increased pressure, a portion of the mixture 30 within the chamber 630 can be forced through the filter 660 and dispensed from the outflow port 690. At least a portion of the mixture 30 can be retained within the chamber 630. For example, the cellular components that are too large to fit through the filter 660 can be retained within the chamber 630, while the plasma passes through the filter 660 and the outflow port 690. In another embodiment, shown in FIG. 21B, sample device 600 comprises a skirt 693 surrounding outflow port 690, the skirt configured to engage with an external docking station or sample receiving zone, such as receptacle 810. The fluid mixture in the chamber of the sample device is dispensed by applying a directional force to the sample device, or to the attached container, to engage or actuate a mechanism to release the mixture. In one embodiment, the directional force is, with respect to a gravitational frame of reference, a downward force. The downward applied force effects release of the fluid mixture from the sample device. Mechanisms responsive to a downward force applied by a user are referred to as "press and release" or "press to dispense" mechanisms. In one embodiment, dispensing mixture from chamber 630 comprises applying a directional force to effect release of mixture, wherein substantially all of the mixture in the chamber is dispensed. In other embodiments, greater than 90%, 95%, 98% or 99% of the mixture in the chamber is dispensed.

Figure 22:
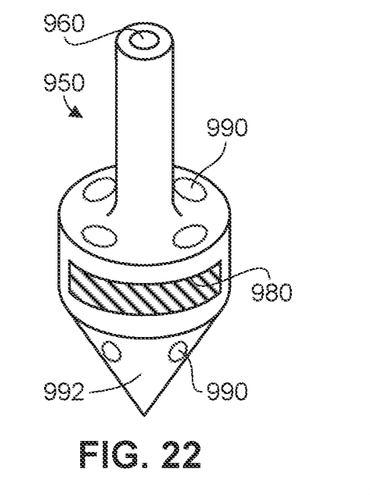
FIG. 22 illustrates a perspective view of a sample device, according to some embodiments of the present disclosure.
Figure 23:
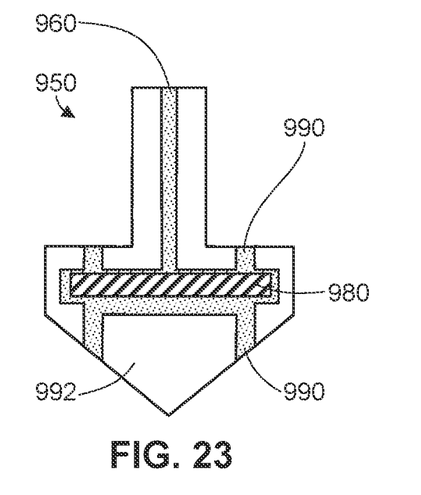
FIG. 23 illustrates a sectional view of the sample device of FIG. 22, according to some embodiments of the present disclosure.

A system can facilitate whole blood separation and dispensation of the plasma while the cellular components are retained. The system can include a sample device for receiving and treating a sample from a patient. FIGS. 22 and 23 illustrate a sample device 950, according to some embodiments of the present disclosure. According to some embodiments, for example as illustrated in FIGS. 22 and 23, the sample device 950 can include an inflow chamber 960 for receiving a sample. The inflow chamber 960 can include a capillary tube with an open end located on a first side of the sample device 950. The inflow chamber 960 can be separated from and/or divide channels 990 with a pad 980. The pad 980 can include an anti-RBC reagent that is configured to facilitate collection of blood cells therein. The channels 990 can provide access to the pad 980 on one or more sides of the pad 980. As described further herein, the channels 990 provide a pathway for reagents after activating the sample device 950 within a container holding the reagents.

Figures 24, 25, 26:
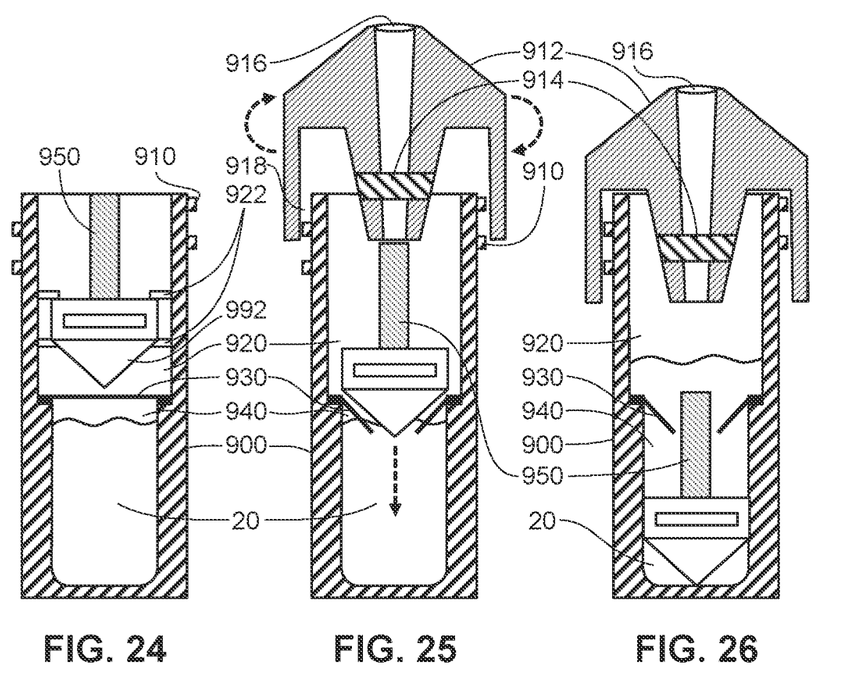
FIGS. 24-26 illustrate sectional views of the sample device of FIG. 22 and a container, according to some embodiments of the present disclosure.

The system can include a container that helps facilitate mixing of a sample with a reagent. FIGS. 24-26 illustrate a container 900, according to some embodiments of the present disclosure. According to some embodiments, for example as illustrated in FIG. 24, the container 900 can include a reservoir 940 for holding and/or receiving a reagent 20, such as a solution containing a buffer. The reservoir 940 can be sealed, at least in part, with a barrier 930, such as a foil cover. The barrier 930 can isolate the reservoir 940 from a chamber 920 of the container 900 until the barrier 930 is punctured, broken, or removed.

The sample device 950 can be placed at least partially within the container 900. For example, the container 900 can include protrusions 922 that can secure at least a portion of the sample device 950. For example, one or more protrusions 922 can be placed on opposing sides of a portion of the sample device 950, such that the sample device 950 is secured within the container 900 until an external force moves the sample device 950 past one or more of the protrusions 922.

A method can employ components of the system or kit, as described herein, to achieve whole blood separation. According to some embodiments a sample, such as blood, can be collected with and into the inflow chamber 960 of the sample device 950. The sample device 950, while secured within the container 900, can be held horizontally or substantially horizontally during filling of the inflow chamber 960.

According to some embodiments, for example as illustrated in FIG. 24, the sample device 950 can be positioned vertically with the inflow chamber 960 gravitationally above the pad 980. While the sample device 950 is in such a position, the sample can be allowed to drain from the inflow chamber 960 and to the pad 980 and/or the channels 990 (e.g., via the pad 980). As the sample passes through the pad 980, the sample can react with substances within the pad 980, such as anti-RBC reagents. For example, at least a portion of the sample can be separated from a second portion of the sample by retaining the second portion at a pad 980. The sample device 950 can be held vertically for an amount of time sufficient to allow the sample to drain out of this inflow chamber 960 (e.g., 10 seconds, 20 seconds, 30 seconds, 40 seconds, 50 seconds, 60 seconds, or more than 60 seconds).

According to some embodiments, for example as illustrated in FIGS. 24-26, the sample device 950 can be advanced within the container 900 to release a reagent. For example, an end 992 of the sample device 950 can puncture the barrier 930 and be at least partially inserted into the reservoir 940 of the container 900. The sample device 950 can be advanced by overcoming a force provided by the one or more protrusions 922 that support the sample device 950. For example, a dispenser 912 can be used to advance the sample device 950. A dispenser interface 918 can engage a container interface 910 to seal a space (e.g., the chamber 920) within the container 900. For example, the container 900 can include the container interface 910 (e.g., threads) that can facilitate connection and securement of the container 900 to the sample device 950. The sample device 950 can be connected to the container 900 by engaging the dispenser interface 918 with the container interface 910. While engaged, the dispenser interface 918 and the container interface 910 maintain a connection between the dispenser 912 and the container 900. The dispenser interface 918 and the container interface 910 can also seal a space within the container 900 so that materials within the space are separate from an external environment. As the dispenser 912 is attached, it can apply a force to the sample device 950 to urge the end 992 of the sample device 950 through the barrier 930. In such a configuration, the reagent 20 is allowed to mix with the sample within the pad 980. For example, the reagent 20 can travel within the channels 990 to access the pad 980 and/or the chamber 920.

According to some embodiments, the sample device 950 and the container 900 can be agitated and/or shaken to mix at least a portion of the sample in the sample device 950 with at least a portion of the reagent 20 in the container 900. The mixing can occur, at least in part, within the channels 990. Within the channels 990, the reagents can mix with the sample that is on or within the pad 980. The sample device 950 and the container 900 can be agitated and/or shaken manually or by a machine.

According to some embodiments, the mixture produced by the agitation and/or shaking can be dispensed from the sample device 950 and the container 900 via the dispenser 912. An outflow port 916 of the dispenser 912 can be directed toward a receptacle of a cassette (not shown). At least a portion of the container 900 can be deformed to create pressure within the channels 990. In response to this increased pressure, a portion of the mixture within the container 900 can be forced through a filter 914 of the dispenser 912 and dispensed from the outflow port 916. The filter 914 can include, for example, glass fibers, and be configured to allow passage of plasma there through while retaining cellular components of the sample. At least a portion of the mixture can be retained within the channels 990. For example, the cellular components that are too large to fit through the filter 914 can be retained within the channels 990 while the plasma passes through the filter 914 and the outflow port 916. In some embodiments, the filter 914 is not included, and the cellular components are retained within the pad 980.

According to embodiments, a kit of parts can include components of the system. For example, one or more kits of parts can include the sample device 950, the container 900, and the dispenser 912. Directions for use ("DFU") can be included with the kit. One or more of the sample device 950, the container 900, and the dispenser 912 can be disposable and packaged for one-time use.

EXAMPLES

A study was performed to evaluate the use of the described whole blood separation device with finger stick whole blood compared to the serum and plasma testing methods using the FDA-cleared. SOFIA® Lyme FIA test device from Quidel Corporation. This prospective study was performed using matched blood specimens (finger stick and serum/plasma) samples collected from 529 subjects suspected of and exhibiting symptoms of Lyme disease across 11 sites located in Lyme endemic regions throughout the United States. The whole blood sampling and Lyme immunoassay were performed immediately at each of the 11 clinical sites by CLIA-waived operators, which demonstrates the ease of use in the hands of non-trained operators. The predicate Lyme IgM and IgG assays and western blot Lyme IgM and IgG assays were performed at centra(reference laboratories that were different from the CLIA-waived testing sites. First tier results of the whole blood separation device with finger stick whole blood compared to no separation device plasma and serum using the SOFIA® Lyme IgM and IgG assay are shown in Tables 1 and 2. There is no statistical difference (p>0.05) between conditions, indicating that the whole blood separation device performs as well as the tests run with plasma and serum.

TABLE 1

Comparison of a whole blood separation device (finger stick whole blood) to no separation device (plasma and serum) using the SOFIA ® Lyme IgM FIA prospective study positive and negative results.

IgM Results (Sofia)

|  | Separation Device (Finger stick blood) | No Sep Device (Plasma) | No Sep Device (Serum) |
| --- | --- | --- | --- |
| Positive | 238 | 243 | 241 |
| Negative | 291 | 286 | 288 |

TABLE 2

Comparison of a whole blood separation device (finger stick whole blood) to no separation device (plasma and serum) using the Sofia Lyme IgG FIA prospective study positive and negative results.

IgG Results (SOFIA ®)

|  | Separation Device (Finger stick blood) | No Sep Device (Plasma) | No Sep Device (Serum) |
| --- | --- | --- | --- |
| Positive | 203 | 198 | 192 |
| Negative | 326 | 331 | 337 |

Clinical performance was evaluated based on a comparison of the Sofia Lyme FIA results when testing capillary whole blood to those obtained by three different Tier 1 IgM and IgG comparator methods testing a matched serum or plasma specimen. The SOFIA® Lyme IgM and IgG percent positive and percent negative agreement to the comparator test devices were evaluated using the whole blood separation device with finger stick whole blood compared to no separation device plasma and serum. This data is presented in Tables 3 and 4. There is no statistical difference (p>0.05) between conditions, indicating that the whole blood separation device performs as well as the tests run with plasma and serum.

TABLE 3

Comparison of whole blood separation device (finger stick whole blood) to no separation device (plasma and serum) using the SOFIA ® Lyme IgM FIA prospective study percent positive and percent negative agreement to the first Tier comparator methods.

IgM Agreement to Comparators (SOFIA ®)

|  | Separation Device (Finger stick blood) | No Sep Device (Plasma) | No Sep Device (Serum) |
| --- | --- | --- | --- |
| % Positive Agreement | 79% | 79% | 79% |
| % Negative Agreement | 73% | 71% | 72% |

TABLE 4

Comparison of whole blood separation device (finger stick whole blood) to no separation device (plasma and serum) using the SOFIA ® Lyme IgG FIA prospective study percent positive and percent negative agreement to the first Tier comparator methods.

IgG Agreement to Comparators (SOFIA ®)

| | Separation Device (Finger stick blood) | No Sep Device (Plasma) | No Sep Device (Serum) |
|---|---|---|---|
| % Positive Agreement | 90% | 89% | 89% |
| % Negative Agreement | 81% | 82% | 84% |

Follow-up second tier testing with IgM and IgG Western blots was performed on all first tier positive results. Second Tier results Were evaluated using the whole blood separation device with finger stick whole blood compared to no separation device plasma and serum. This data is presented in Table 5. There is no statistical difference (p>0.05) between conditions for both IgM and IgG second tier positive results, indicating that the whole blood separation device performs as well as the tests run with plasma and serum.

TABLE 5

Comparison of a whole blood separation device (finger stick whole blood) to no separation device (plasma and serum) using the SOFIA ® Lyme IgM and IgG FIA prospective study results that are confirmed positive by Western Blot.

Second Tier Western Blot Confirmation

| | Separation Device (Finger stick blood) | No Sep Device (Plasma) | No Sep Device (Serum) |
|---|---|---|---|
| IgM Positive Results | 106 | 105 | 106 |
| IgG Positive Results | 72 | 73 | 71 |

Follow-up second tier testing with IgM and IgG Western blots was performed on first tier positive results generated with the SOFIA® whole blood separation device and all comparator methods that did not use the whole blood separation device. For Lyme IgM, the results demonstrate that there are more second tier positive results using the SOFIA® whole blood separation device (106) compared to the comparator methods (positive results range between 77-95). This means that there are more suspected Lyme positive patients in the early stage of disease that will be diagnosed using the SOFIA® IgM whole blood method. For Lyme IgG, the results demonstrate that there are a similar number of second tier positive results using the Sofia whole blood separation device (72) compared to the comparator methods (positive results range between 57-72). This means that in some cases there are more suspected Lyme positive patients that will be diagnosed using the SOFIA® IgG whole blood method. The results are summarized in Table 6.

TABLE 6

Comparison of a whole blood separation device (finger stick whole blood) to no separation device (plasma and serum) using the SOFIA ® Lyme IgM and IgG FIA prospective study results that are confirmed positive by Western Blot.

Second Tier Western Blot Confirmation

| Test Method | IgM Positive Results | IgG Positive Results |
|---|---|---|
| Sofia Sep Device (Finger stick blood) | 106 | 72 |
| Biorad (Serum) | 82 | 72 |
| Trinity (Serum) | 80 | 57 |
| Zeus (Serum) | 95 | 72 |
| Vidas (Serum) | 77 | 70 |

The described whole blood separation device has a number of advantages over the traditional serum and plasma method. For example, the described whole blood separation allows a small sample volume (25 ul blood from a finger stick instead of large volume drawn from venipuncture tube). By further example, the described whole blood separation allows quick turn-around time (<60 seconds) compared to centrifugation (>15 min). By further example, the described whole blood separation allows ease of use compared to centrifugation, thereby allowing use by CLIA waived operators instead of trained lab operators. By further example, the described whole blood separation requires no additional equipment, providing a single-use separation device instead of lab instruments, such as a centrifuge. By further example, the described whole blood separation provides similar first tier performance compared to serum and plasma Lyme IgM and IgG results. By further example, the described whole blood separation provides improved second tier performance compared to traditional methods for Lyme IgM and IgG.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A device comprising:
   an inflow chamber for receiving a fluid sample;
   a mixing chamber;
   a pad between the inflow chamber and the mixing chamber, the pad comprising a processing reagent;
   an outflow port adjacent to the mixing chamber; and
   an interface for sealably connecting the device to a container;
   wherein the container comprises a reservoir and the interface for sealably connecting the device to the container is configured such that the reservoir is in fluid communication with the mixing chamber through a channel formed between the interface and the pad, wherein the channel provides a pathway for reagents from the container to the mixing chamber.

2. The device of claim 1, wherein the inflow chamber comprises a capillary tube.

3. The device of claim 2, wherein the capillary tube has a length selected to collect a fixed volume of fluid sample.

4. The device of claim 1, wherein the sample device further comprises a filter between the mixing chamber and the outflow port.

5. The device of claim 1, further comprising a buffer solution within the reservoir.

6. The device of claim 1, wherein the processing reagent is a red blood cell agglomerating substance.

7. A kit comprising: the device of claim 1 and a collection device.

8. The kit of claim 7, further comprising the container.

9. A device comprising:
   an inflow chamber comprising a pad for receiving a liquid sample; and
   a mixing chamber having an outflow port;
   wherein the device is configured to sealably connect to a container, said container comprising:
   a reservoir configured to contain or containing reagents; and
   an interface for sealably connecting the device to the container such that the reservoir is in fluid communication with the mixing chamber through a channel formed between the interface and the pad, wherein the channel provides a pathway for the reagents from the container to the mixing chamber.

10. The device of claim 9, further comprising a collection device for collecting the liquid sample.

11. The device of claim 10, wherein the collection device comprises a capillary tube and a bulb in fluid communication with the capillary tube.

12. The device of claim 9, wherein the pad comprises a processing reagent.

13. The device of claim 12, wherein the processing reagent is a red blood cell agglomerating substance.

14. A kit comprising: the device of claim 9 and a collection device.

15. The kit of claim 14, further comprising the container.

* * * * *